US006545144B2

(12) United States Patent
Kolzau et al.

(10) Patent No.: US 6,545,144 B2
(45) Date of Patent: Apr. 8, 2003

(54) METHOD FOR ISOLATING NUCLEIC ACIDS FROM A LIQUID SAMPLE CONTAINING NUCLEIC ACIDS

(75) Inventors: Thomas Kolzau, Hamburg (DE); Wilhelm Plüster, Hamburg (DE); Mathias Ulbricht, Berlin (DE)

(73) Assignee: Eppendorf AG, Hamburg (DE)

( * ) Notice: Subject to any disclaimer, the term of this patent is extended or adjusted under 35 U.S.C. 154(b) by 0 days.

(21) Appl. No.: 10/066,509

(22) Filed: Jan. 30, 2002

(65) Prior Publication Data

US 2002/0110829 A1 Aug. 15, 2002

(30) Foreign Application Priority Data

Feb. 10, 2001 (DE) .......................... 101 06 199

(51) Int. Cl.$^7$ .................. C07H 21/00; G01N 30/00; G01N 30/48
(52) U.S. Cl. ............... 536/25.4; 536/25.41; 536/25.42; 435/69.1; 435/320; 435/272; 422/70; 422/101
(58) Field of Search .................. 435/270, 69.1, 435/320; 536/25.4, 25.41, 25.42, 23.5; 422/70, 101

(56) References Cited

U.S. PATENT DOCUMENTS 5,804,684 A * 9/1998 Su .......................... 536/25.4

FOREIGN PATENT DOCUMENTS

WO    WO 99/23487    * 11/1998

OTHER PUBLICATIONS

Qiagen Plasmid Purification Handbook, "Qiagen Plasmid Midi and Maxi Protocol," Sep. 2000, pp. 15–19.*

* cited by examiner

Primary Examiner—James Ketter
Assistant Examiner—Maria Marvich
(74) Attorney, Agent, or Firm—Sidley Austin Brown & Wood, LLP

(57) ABSTRACT

A method for the isolation of nucleic acids from a liquid sample, which contains nucleic acids, using a filtering device, which has pores, through which the sample is allowed to flow in the course of the isolation, the nucleic acids, and contained in the sample, being retained selectively in or at the pores, wherein the sample is mixed with a concentration of the precipitating agent for nucleic acids, which is sufficient to condense the nucleic acids and the sample is then allowed to flow through the filtering device, the pores of the filtering device used having inner wall regions with variable surface structures, which are constructed differently depending on the medium passed through the pores and by which the permeability of the pores can be adjusted between a state, in which the condensed nucleic acid molecules are retained, and a state, in which the dissolved nucleic acid molecules can pass through.

1 Claim, 1 Drawing Sheet

1  2  3  4  5

1 2 3 4 5 6 7 8 9 10 11 12 13 14 15 16 17 18 19 20

1 2 3 4 5 6 7 8 9 10 11 12 13 14 15 16 17 18 19

METHOD FOR ISOLATING NUCLEIC ACIDS FROM A LIQUID SAMPLE CONTAINING NUCLEIC ACIDS

CONTINUING DATA

This application claims priority to foreign application Germany 101 06 199.4, filed Feb. 10, 2001.

FIELD OF INVENTION

The invention relates to a method by which nucleic acids are isolated at flow-through filtering devices which, for example, have pores. For the isolation, a liquid sample, containing the nucleic acids, is allowed to flow through the filter device, the nucleic acids being retained in or at the pores. Usually, the filtering devices are then washed and the nucleic acids are eluted for further use in the next step.

BACKGROUND INFORMATION AND PRIOR ART

Known methods use ion exchangers, for example, as filtering devices. Under low-salt conditions, the nucleic acid molecules are bound. Elution takes place under high-salt conditions, which make the further use of the eluted nucleic acid molecules difficult or usually requires a dialysis to be interposed.

Likewise, the use of filter materials, based on silica, in conjunction with binding buffers, which contain chaotropic reagents, is known. The chaotropic reagents bring about specific binding of nucleic acids to the silica materials. Admittedly, it is possible to elute once again under low-salt conditions here. However, it is a disadvantage that the chaotropic reagents are relatively aggressive, so that the working up is not problem-free.

It is furthermore possible to use molecular sieves. The disadvantage here is that, during the elution, the nucleic acids cannot be sucked through the molecular sieve in the original filter device. Instead, they must be eluted on the side on which they entered the molecular sieve. This usually means an additional step and, accordingly, prolongs the working-up time.

OBJECT OF THE INVENTION

It is therefore an object of the invention to provide a method with which the disadvantages named above can be avoided.

Figure 1:
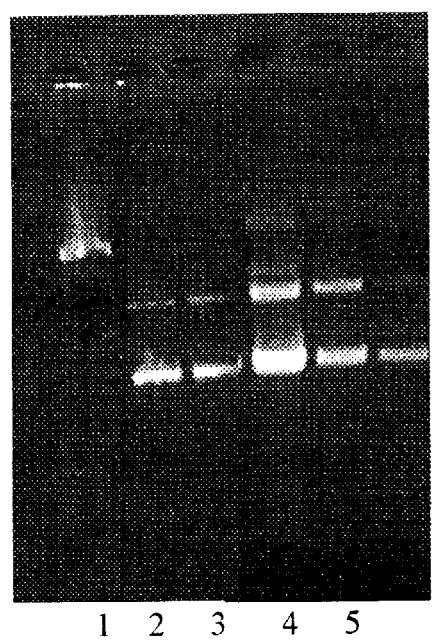
FIG. 1 is an agarose gel that shows the result of filtering DNA through an unmodified or modified filter.

As is known from the state of the art, the inventive method works with a filter device, through the pores of which the sample is allowed to flow in the course of the isolation. In the case of the inventive method, the nucleic acids contained in the sample are also to be retained selectively in or at the pores. In this connection, the filtering device may, in particular, be a filter matrix or a membrane. However, filtering devices with micro-channels are also conceivable. In this case, the concept of pore, used within the scope of this application, is to be understood broadly and should also cover such channel structures.

Pursuant to the invention, provisions are made in this connection so that the sample is mixed in a first step with a precipitating agent (also referred to as binding buffer in the examples) for nucleic acids in a concentration that is sufficient to condense the nucleic acids. Preferably, polyethylene glycol and/or isopropanol are used as the precipitating agent; however, precipitating agents are not limited to these materials. In general, all precipitating agents that can condense nucleic acids are suitable. Suitable concentrations are between 5 and 30% for PEG and between 10 and 100% for isopropanol.

Condensation is understood to be the conformational changes, which are brought about by external circumstances, and comprise compressions of the nucleic acid molecule up to the insoluble state. The compression of the nucleic acid molecule is associated with a decrease in flexibility and an increase in complexity of the molecular structure. Thus, though the nucleic acids remain soluble, they are less flexible and more bulky than in a fully soluble state.

The condensation brought about by the precipitating agent leads to an increase in volume of nucleic acids and, at the same time, to a decrease in flexibility. As mentioned above, plasmids, for example, tend to assume a compressed confirmation in the presence of, for example, PEG or isopropynol.

In the next step, the mixture of sample and precipitating agent is then forced or sucked through the filtering device. This can be accomplished, in particular, by centrifugation or vacuum filtration.

The pores of the filtering device used are constructed so that they retain the condensed nucleic acid molecules selectively. On the other hand, during the elusion, for example, the pores permit the completely dissolved (not condensed) nucleic acid molecules to pass through. It should be noted here that all data that relates to the retention of nucleic acids in or at the pores or to their passage through the pores, is static data. For example, when it is stated that the pores are permeable to nucleic acids, this applies to at least a predominant portion of the pores as well as of the nucleic acids contained in the sample (but not necessarily to all pores and all nucleic acids). Of course, it cannot be excluded that some pores become clogged because of a deep-bed filter effect, etc., and that passage through the pores is then no longer possible. On the other hand, a deep-bed filter effect can, of course, also support the filtering effect as a whole.

The inventive method can therefore be carried out very easily. After the sample containing the nucleic acids is mixed with the precipitating agent, the sample is sucked, for example, with vacuum filtration, or pipetted with a direct displacer through a filter device with the previously described pore properties, the condensed nucleic acid molecules being retained in or at the pores.

After optionally interposed washing steps, an elution buffer, which fully dissolves the nucleic acids, is passed through the filtering device. The elution buffer may be a buffer with a low salt concentration and, in the simplest case, is water. The elution buffer only has to be able to cancel the condensed state of the nucleic acid molecules. In the dissolved state, the nucleic acid molecules can then pass through the pores and, are collected purified, on the averted side of the filtering device.

Pursuant to the invention, provisions are made so that the pores of the filtering device have inner wall areas with variable surface structures. These variable surface structures are formed differently depending on the medium passed through the pores, and, in this manner, control the permeability. Usually, one starts out with pore diameters between 0.2 to 20 micrometers. However, it was found that the filtering devices clog at smaller pore diameters. On the other hand, the selective accumulation of nucleic acids in the filtering device suffers at larger diameters. The pore diameters are larger than those of ultra filtration membranes used for molecular sieves.

The variable surface structures are used to adjust the pores to diameters at which the condensed nucleic acid molecules are retained or to diameters at which uncondensed molecules can pass through the pores. The adjustment is usually accomplished by the medium, carrying the sample mixture. These substances, which are addressed further below, may be added separately to the sample or to the sample mixture. However, they may also be contained in the binding buffer or the elution buffer. In the simplest case, the precipitating agent used to condense nucleic acids, also brings about an adjustment of the variable pores to the state in which they retain the nucleic acids. On the other hand, the buffers used for the elution adjust the surface structures of the pores to a permeable state.

Suitable variable surface structures may, for example, be coatings with deprotonatable groups, such as sulfonic acid, phosphoric acid or carboxylic acid groups. It was additionally found that such deprotonatable groups have affinities for nucleic acid molecules, which vary depending on the salt concentration, the pH or the presence of certain reagents, such as PEG or isopropyl, to name only two examples. At low-salt concentrations or at a neutral to alkaline pH or in the absence of special reagents, such as PEG, there is no or only a slight affinity for nucleic acid molecules. If the pH is lowered or the salt concentration increased, the affinity of these groups for nucleic acids is also increased.

Filtering devices with appropriately coated inner wall regions may be particularly advantageous depending on the buffer medium used. In the case of a high-salt buffer, the pores have a high affinity for nucleic acids. In the presence of elution buffers of low salt concentration, the affinity decreases and the nucleic acids can be removed from the filtering device.

It is particularly preferred if the variable surface structures are formed as polymer chains, which, depending on the buffer medium passed through the pores, either protrude in stretched form from the inner wall of the pore or assume a compressed form. By these means, the effective cross section of the pore can be adjusted relatively easily to the desired permeability state. Preferably, polymers of acrylic acid or its derivatives are used as polymer chains.

In particular, when coating with polyacrylic acids, but also generally when coating with the other coatings addressed, a high affinity for nucleic acids can also be obtained, for example, by means of PEG or isopropanol. In the case of the polymer chains, PEG causes the chains to have a compressed form, in which they retain condensed nucleic acids particularly effectively. The permeable, stretched state of the polymer chains can be restored, for example, under low salt conditions (water).

The development addressed above is particularly advantageously, since, by using PEG, the permeability of the pores can be adjusted and, at the same time, the condensation of the nucleic acid molecules brought about with one component.

The inventive method can be used preferably for plasmids or PCR products. However, the purification of genomic DNA or RNA is also conceivable. In cases of doubt, the filtering devices used must be matched, with respect to their pore size or buffer conditions to the PCR products, which are to be expected.

In the following examples, the invention is explained in greater detail

EXAMPLE 1

Purification of Plasmid DNA Using Filters

Samples which contained the plasmid pBlueSchript SK were investigated. For preparing the samples, 1.5 mL of a bacterial culture (DH10B) were centrifuged. To lyse the cells, the pellet was mixed with the P1–P3 buffers (P1; 100 $\mu$L, P2: 300 $\mu$L, P3: 300 $\mu$L from the "Perfect Prep Plasmid Midi" kit of Fa. Eppendorf and centrifuged once again. The lysate was mixed with 700 $\mu$L of binding buffer (20% PEG, 1.5 molar sodium chloride) and forced through the following different filter materials by centrifugation:

1) Cellpore C2 (Fa. Esters, Aachen), 2 mm thick, 3 $\mu$m nominal pore width
2) The above filter, coated with polyacrylic acid The filter (Cellpore C2) of 1) above was modified by equilibrating it with shaking for 2 hours with a 100 mM solution of benzophenone (BP) in acetone. Subsequently the filter was coated with a 10% aqueous solution of acrylic acid and then illuminated for 15 minutes with UV radiation (UVA Spot 2000, Dr. Hönle GmbH, Planegg). The modified filter was then extracted for 24 hours at 60° C. with water and dried. After passage of the sample, the filter was washed with 400 $\mu$L of a 75% ethanolic solution, after which it was eluted with 70 $\mu$L of water. The yield of plasmid in the eluate was determined by gel electrophoresis. The result is shown in FIG. 1.

A control was applied in track 1. Tracks 2 and 3 show the results when different uncoated filters are used. Tracks 4 and 5 show the results when coated filters are used.

It can be seen that the plasmids are cleaned up much better with the modified filter variant (see, in particular, track 4) than with unmodified filters (tracks 2 and 3), which were tested for comparison.

EXAMPLE 2

Cleaning Up PCR Products on Micro-filter Plates. (384 Format)

PCR product samples (250 bp and 400 bp; bp=base pair) were investigated. In each case, 8 $\mu$L of the sample was mixed with 80 $\mu$L of different binding buffers and then forced through modified micro-filter plates (384 format) by means of centrifugation.

The following binding buffers were used:
1) 10% PEG 8000, 1.5 M NaCl
2) 10% PEG 8000, 1.5 M NaCl, 0.01 M $MgCl_2$
3) 8% PEG 8000, 1.2 M NaCl, 20% isopropanol
4) 60% isopropanol, 0.2 M NaCl The modification was carried out as described above and the modified filters were placed in the cavities of the plates.

Figure 2:
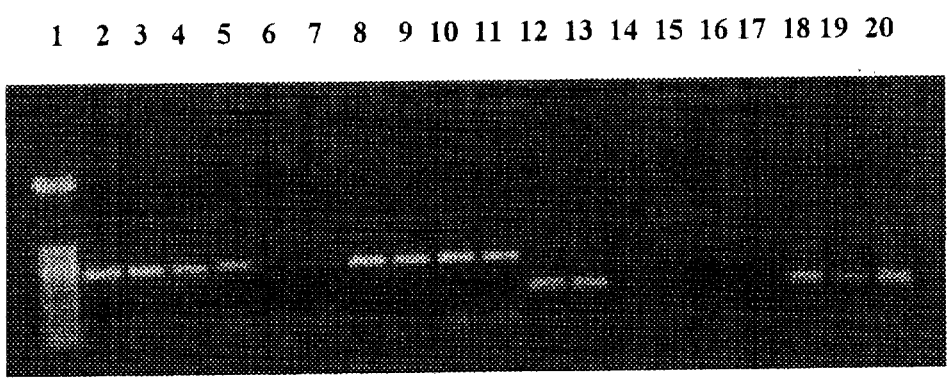
FIG. 2 is an agarose gel that shows the effect on purification of different binding buffers for 400 and 250 bp PCR fragments.

After passage of the sample, the filters used were washed in each case with 70 $\mu$L of a 75% ethanolic solution, and then eluted with 10 $\mu$L of water. The total yield in the eluate (10 $\mu$L) was determined by gel electrophoresis and the result is shown in FIG. 2.

Track 1: control; tracks 2 and 3: control 400 bp; tracks 4 and 5: sample 400 bp with binding buffer 1; tracks 6 and 7: sample 400 bp with binding buffer 2; tracks 8 and 9, sample 400 bp with binding buffer 3; tracks 10 and 11: sample 400 bp with binding buffer 4; tracks 12 and 13: control 250 bp; tracks 14 and 15: sample 250 bp with binding buffer 1;

tracks 16 and 17: sample 250 bp with binding buffer 2; tracks 18 and 19: sample 250 bp with binding buffer 3; track 20: sample 250 bp with binding buffer 4.

It can be seen that different yields are obtained, depending on the binding buffer used and the size of the products. Good results can be achieved for 400 bp products with binding buffers 1, 3 and 4. When binding buffer 2 is used, recognizable bands cannot be obtained. With 250 bp products, good results are achieved with binding buffers 3 and 4. On the other hand, when binding buffers 1 and 2 are used, the bands, if they can be recognized at all, are only weak.

EXAMPLE 3

Cleaning Up PCR Products Using Micro-Filter Plates (96 Format)

Samples with PCR products (400 bp) were investigated.

In each case, 20 µL of the sample was mixed with 200 µL of a binding buffer 1–4, given in Example 2, and forced through modified and unmodified micro-filter plates (96 format) by means of centrifugation.

The plates were retained in the cavities by inserting modified or unmodified filter materials. The modification was carried out as described in Example 1.

Figure 3:
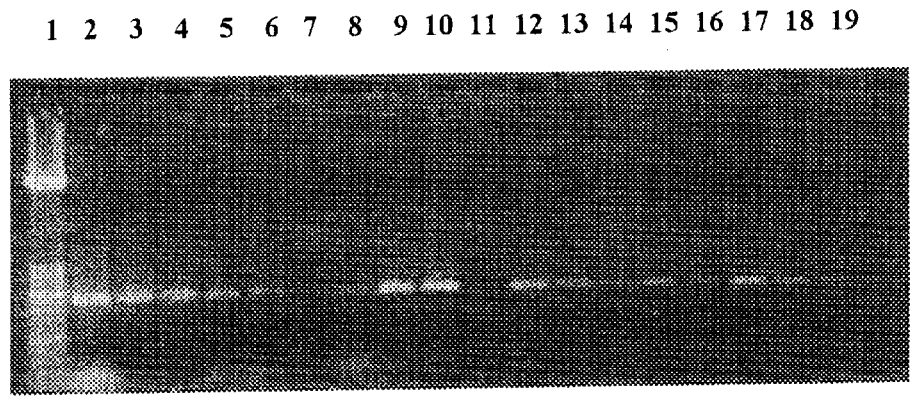
FIG. 3 is an agarose gel that shows the effect on purification of different binding buffers and filters for 400 bp PCR fragments.

After passage of the sample, the micro-filter plates where washed with 200 µL of a 75% ethanolic solution and then eluted with 20 µL of water. The yield was determined in 10 µL of eluate by gel electrophoresis. The result is shown in FIG. 3.

Track 1: control; track 2: control, PCR batch 400 bp, not cleaned up; tracks 3 and 4: control, conventionally purified PCR product 400 bp; tracks 5 and 6: sample 400 bp with binding buffer 1, modified filter, tracks 7 and 8: sample 400 bp with binding buffer 2, modified filter; tracks 9 and 10: sample 400 bp with binding buffer 3, modified filter; tracks 11 and 12: sample 400 bp with binding buffer 4, modified. filter; tracks 13 and 14: sample 400 bp with binding buffer 1, unmodified filter; tracks 15 and 16: sample 400 bp with binding buffer 2, unmodified filter; tracks 17 and 18: sample 400 bp with binding buffer 3, unmodified filter, track 19: sample 400 bp with binding buffer 4, unmodified filter.

It can be seen that especially binding buffer 3 (8% PEG, 1.5M NaCl, 20% isopropyl alcohol) is suitable when the modified filter is used. The unmodified filters, which were tested for comparison, admittedly produced yields, which are recognizable in the gel. However, the yields are less than in the case of modified filters.

What is claimed is:

1. A method for the isolation of nucleic acids from a liquid sample containing nucleic acids, using a filtering device with pores through which the sample is allowed to flow in the course of the isolation, the nucleic acids contained in the sample being retained selectively in or at the pores and ultimately eluted comprising the mixing of a sample with a concentration of the precipitating agent for nucleic acids sufficient to condense the nucleic acids, the filtering of the sample through the filtering device, the pores of such filtering device having inner wall regions with variable surface structures composed of polymer chains where one end of such polymer chain is bound to the inner wall region of the pore and the other end of which is freely movable, such variable surface structures allowing the permeability of the pores to be adjusted between a state, in which the condensed nucleic acid molecules are retained, and a state, in which the dissolved nucleic acid molecules can pass through, eluting the nucleic acids with a suitable elution buffer.

* * * * *